United States Patent [19]
Askin et al.

[11] Patent Number: 5,618,939
[45] Date of Patent: Apr. 8, 1997

[54] PROCESS FOR MAKING HIV PROTEASE INHIBITORS

[75] Inventors: David Askin, Warren; Paul Reider; Kai Rossen, both of Westfield; Richard J. Varsolona, Scotch Plains; Ralph P. Volante, Cranbury; Kenneth M. Wells, Somerville, all of N.J.

[73] Assignee: Merck & Co., Inc., Rahway, N.J.

[21] Appl. No.: 474,926

[22] Filed: Jun. 7, 1995

Related U.S. Application Data

[63] Continuation of Ser. No. 341,334, Dec. 16, 1994, abandoned, which is a continuation of Ser. No. 92,627, Jul. 16, 1993, abandoned.

[51] Int. Cl.$^6$ .............. C07D 409/06; C07D 409/14; C07D 405/06; C07D 241/04
[52] U.S. Cl. .............. 544/368; 544/137; 544/360; 544/364; 544/373; 544/374; 544/390; 546/146; 546/147; 548/217; 549/552
[58] Field of Search .................... 546/146, 147; 544/364, 360, 373, 349, 390, 368, 374; 548/217

[56] References Cited

U.S. PATENT DOCUMENTS

| | | | |
|---|---|---|---|
| 5,026,853 | 6/1991 | Van Daele et al. | 544/390 |
| 5,075,337 | 12/1991 | Cordi et al. | 544/390 |
| 5,169,952 | 12/1992 | Askin et al. | 544/137 |
| 5,218,114 | 6/1983 | Bock et al. | 540/509 |
| 5,461,154 | 10/1995 | Jungheim et al. | 544/360 |
| 5,463,067 | 10/1995 | Askin et al. | 548/113 |
| 5,484,926 | 1/1996 | Dressman et al. | 546/114 |
| 5,491,238 | 2/1996 | Askin et al. | 544/368 |

FOREIGN PATENT DOCUMENTS

| | | |
|---|---|---|
| 541168 | 5/1989 | European Pat. Off. . |
| 0346847 | 6/1989 | European Pat. Off. . |
| 0521686 | 6/1992 | European Pat. Off. . |

OTHER PUBLICATIONS

Askin, D., et al., J. Org. Chem., 1992, 57, 2771–2773.
Baldwin, J.E., et al., J. Chem. Soc., Chem. Commun., 1992, 1249–1251.
Burgess, K., et al., j. Org. Chem. 1992, 57, 5931–5936.
Felder, E., et al., Helvetica Chim. Acta, 1960, 43, 888.
Hanson, R.M., Chem. Rev., 1991, 91, 437–475.
J. Klunder, et al., J. Org. Chem., 1989, 54, 1295–1304.
Kohl, N.E., et al., Proc. Nat'l Acad. Sci., 1988, 85, 4686.
M. Figueredo, et al., Tetrahedron, 1987, 43, 1881–1886.
Pearl, L.H. et al., Nature, 1987, 329, 351.
Pirrung, M.C., et al., Helvetica Chimica Acta, 1989, 72, 1301–1310.
Power, M.D., et al., Science, 1986, 231, 1567.
Ratner, L. et al., Nature, 1985, 313, 277.
Toh, H. et al., EMBO J., 1985, 4, 1267.
Kageyama et al, *Antimicrobial Agents and Chemotherapy*, 36, pp. 926–933 (1992).
Winslow et al, *AIDS*, 8, pp. 753–756 (1994).
Barton et al, Tetrahedron: Asymmetry, 3, pp. 1189–1196 (Sep. 1992).
*Protective Groups in Organic Synthesis* by Theodora Greene, pp. 223–224, 232 (1981).
Canas et al, *Tetrahedron Letters*, 32, pp. 6931–6934 (1991).
Mulzer et al, *Liebigs. Ann. Chem.*, pp. 445–448 (1988).

*Primary Examiner*—Emily Bernhardt
*Attorney, Agent, or Firm*—Mary A. Appollina; Carol S. Quagliato; Melvin Winokur

[57] ABSTRACT

A process is disclosed for making a chiral compound of the formula

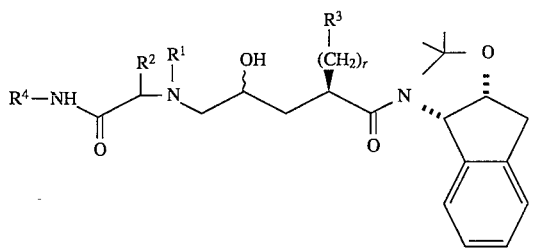

comprising reacting an epoxide compound of the formula

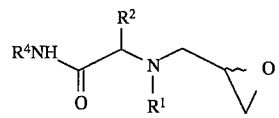

and an amide of the formula

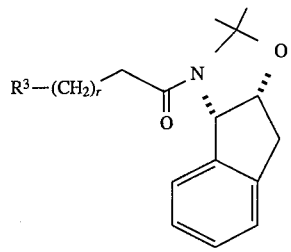

in the presence of a strong base at a low temperature.

11 Claims, No Drawings

PROCESS FOR MAKING HIV PROTEASE INHIBITORS

This is a continuation of application Ser. No. 08/341,334 filed on Dec. 16, 1994 now abandoned which is a continuation of application Ser. No. 08/092,627 filed on Jul. 16, 1993 now abandoned.

BACKGROUND OF THE INVENTION

The present invention is concerned with a novel intermediate and process for synthesizing compounds which inhibit the protease encoded by human immunodeficiency virus (HIV), and in particular L-735,524, or pharmaceutically acceptable salts thereof. These compounds are of value in the prevention of infection by HIV, the treatment of infection by HIV and the treatment of the resulting acquired immune deficiency syndrome (AIDS).

More specifically, the instant process involves the reaction of an amine nucleophile such as a piperazine derivative, with an activated glycidyl derivative such as 2(S)-glycidyl nosylate, to afford epoxide intermediate which is useful in the preparation of HIV promase inhibitor compounds, including L-735,524. Also provided is an improved process for the synthesis of specific dialkylamines used in the synthesis of HIV protease inhibitors.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature virus assembly and function. Inhibition of this processing prevents the production of normally infections virus. For example, Kohl, N. E. et al., Proc. Nat'l Acad. Sci. 85, 4686 (1988) demonstrated that genetic inactivation of the HIV encoded protease resulted in the production of immature, non-infections virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ramer, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. etal., Nature 329, 351 (1987)]. The end product compounds, including L-735,524 which is shown in Example 11 below, that can be made from the novel intermediates and processes of this invention are inhibitors of HIV protease, and are disclosed in EPO 541, 168, which published on May 12, 1993.

Previously, the synthesis of L-735,524 and related compounds was accomplished via a 12-step procedure which employed a hydroxy protected dihydro-5(S)-hydroxymethyl-3(2H)-furanone which was alkylated, and involved :replacement of an alcohol leaving group on the alkylated furanone with a piperidine moiety. The coupled product was then hydrolyzed to open the furanone ring into a hydroxy acid moiety, and the acid was ultimately coupled to 2(R)-hydroxy-1(S)-aminoindane. This procedure is described in EPO 541,168. The extreme length of this route (12 steps), renders this process time consuming and labor intensive, and it requires the use of many expensive reagents and an expensive starting material. A route requiring fewer reaction steps and reagents would provide desirable economical and time-saving benefits.

A modified route to L-735,524 and related compounds was also shown in EPO 541,168 based on the diastereoselective alkylation of the enolate derived from N-(2(R)-hydroxy-1(S)-indan-N,O-isopropylidene-yl)-3-phenyl-propaneamide, in which the $C_3$–$C_5$ three-carbon unit was introduced as an allyl group and later oxidized. Some problems with this route are: (a) four steps are necessary to effect the introduction of the three carbon glycidyl fragment, (b) highly toxic $OsO_4$ is used in the process and (c) low diastereoselectivity is obtained in the dihydroxylation step. Thus, a desirable process would directly introduce the three carbon unit in the correct chiral oxidized form.

Furthermore, the synthesis of the chiral piperazine intermediate was effected from 2-pyrazinecarboxylic acid in a 6 step procedure and required the use of expensive reagents such as BOC-ON and EDC. A shorter route to the piperazine intermediate which also does not use expensive reagents would thus be desired.

Several examples of condensations of stabilized carbanions with glycidol and its derivatives (activated or unactivated) are known in the literature; however, no known methods produce a new epoxide directly in good yield. See, e.g., Hanson, R. M., Chem. Rev., 1991, 91, 437–475. In the case of activated glycidol derivatives and carbon nucleophiles, this is due primarily to the anticipated and undesirable "double" addition of the nucleophile to the epoxide product.

Condensations of stabilized carbanions with activated non-racemic glycidol derivatives have been demonstrated: malonate anion has been coupled with both non-racemic epichlorohydrin i and non-racemic glycidyl triflate ii to afford the cyclopropyl-lactone iii. See, e.g., Pirrung, M. C., et al., Helvetica Chimica Acta 1989, 72, 1301–1310, and Burgess, K., et al., J. Org. Chem. 1992, 57, 5931–5936. Thus, in this case, the intermediate epoxide undergoes further reaction to afford the cyclopropyl ring system. In the case of i, the initial reaction with malonate anion occurs at the epoxide terminus ($C_3$), whereas with ii, the initial reaction occurs at the triflate $C_1$ terminus.

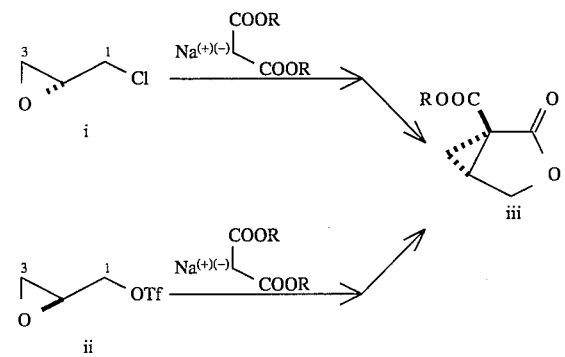

A related example is reaction of sulfone-stabilized carbanion derived from v. with glycidyl tosylate iv to afford the hydroxy-tosylate vi. See, e.g., Baldwin, J. E., et al., J. Chem. Soc. Chem. Commun. 1992, 1249–1251. In this case, although double addition of the carbanion is not a major problem, an additional step is necessary to convert the intermediate hydroxy-tosylate vi to the desired epoxide vii.

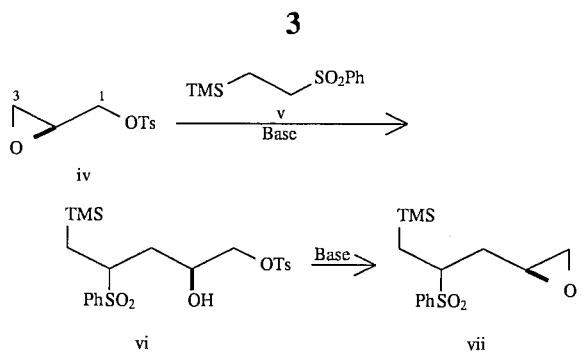

Similarly, it is unknown in the literature and unexpected that nitrogen nucleophiles can be selectively added to activated glycidol derivatives in good yield without the problematic double addition.

Also known in the art is the condensation of amide enolates derived from N-(2(R)-hydroxy-1(S)-indan-N,O-isopropylidene-yl)-3-phenylpropaneamide 7 with protected alpha-amino epoxides viii to afford the desired hydroxyethylene dipeptide isostere intermediates ix with a high degree of stereocontrol for the $C_2$-(R)-stereocenter. See, e.g., Askin, D., et al., *J. Org. Chem.*, 1992, 57, 2771–2773 and U.S. Pat. No. 5,169,952 to Askin, D., et al. After hydrolysis, the deprotected hydroxyethylene dipeptide isostere inhibitors are obtained.

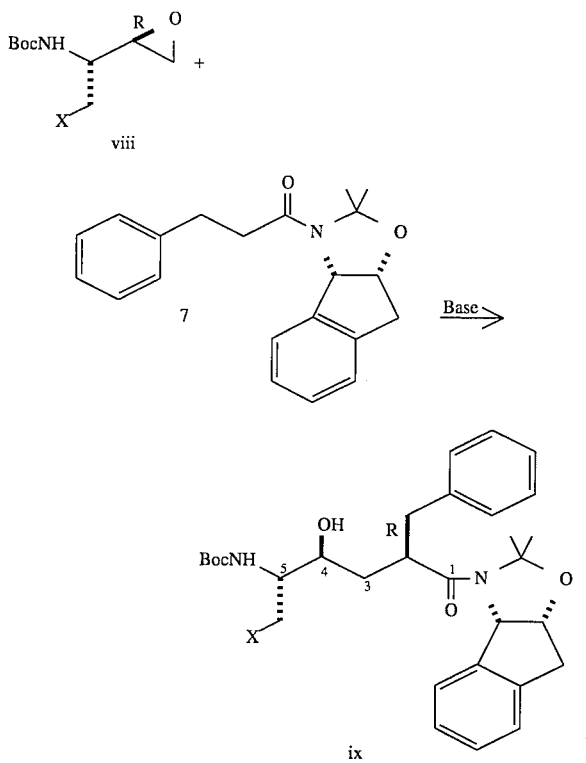

The resolution of 2-piperazinecarboxylic acid with (+)-CSA is known. See. e.g., Felder, E., etal., *Helvetica Chim. Acta*, 1960, 43,888. However, examples of the resolution of piperazine amides are not known in the literature.

The instant invention provides a more advantageous method for preparing HIV protease inhibitors than previously known. It allows a much shorter, more highly diastereoselective, higher yielding synthesis of the compounds disclosed in EPO 541,168, and in particular L-735,524, without the use of toxic reagents such as osmium tetraoxide or expensive reagents such as (S)-(+)-dihydro-5-(hydroxymethyl)-(2(3H)-furanone.

SUMMARY OF THE INVENTION

The instant invention involves novel synthetic methods for making amino-epoxide intermediates such as 3, which are useful for the synthesis of HIV protease inhibitors. One embodiment of the invention involves the reaction of an amine nucleophile such as 1 with an activated glycidol derivative such as 2(S)-glycidyl nosylate 2, to afford an epoxide product such as 3 in good yield. The result of this reaction is unexpected since epoxide 3 was predicted to undergo further reaction under the coupling conditions to afford a large amount of dimer product 3-a, thus giving poor yields of 3.

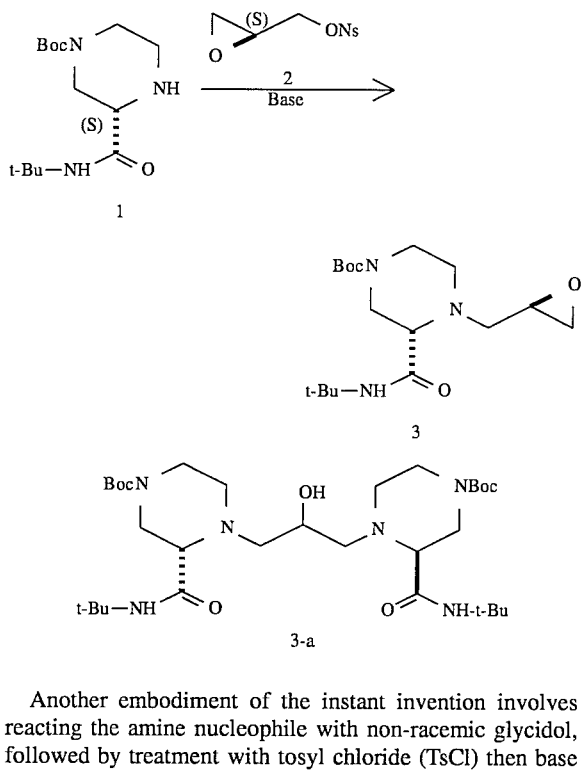

Another embodiment of the instant invention involves reacting the amine nucleophile with non-racemic glycidol, followed by treatment with tosyl chloride (TsCl) then base to obtain the amino-epoxide intermediate.

Still another embodiment involves the reaction of the amino-epoxide intermediate with an amide of formula VIII, defined below, to produce intermediates of formula I, defined below.

A further embodiment of the instant invention involves novel routes for obtaining compound 1 in the desired chiral configuration. This can be accomplished efficiently and in high yield by treatment of racemic 2-tert-butyl-carboxamide piperizine with (+)-CSA or L-PGA followed by crystallization of the chiral product, which is then protected with $BOC_2O$. Alternatively, the compound 1 is obtained by kinetic methods.

Some abbreviations that may appear in this application are as follows.

ABBREVIATIONS

| Designation | |
|---|---|
| | Protecting Group |
| BOC (Boc) | t-butyloxycarbonyl |
| CBZ (Cbz) | benzyloxycarbonyl (carbobenzoxy) |
| TBS (TBDMS) | t-butyl-dimethylsilyl |
| | Activating Group |
| Ts or tosyl or tosylate | p-toluenesulfonyl |
| Ns or nosyl or nosylate | 3-nitrobenzenesulfonyl |
| Tf or triflyl or triflate | trifluoromethanesulfonyl |
| Ms or mesyl or mesylate | methanesulfonyl |
| | Coupling Reagent |
| BOP reagent | benzotriazol-1-yloxytris (dimethylamino)-phosphonium hexafluorophosphate |
| BOP-Cl | bis(2-oxo-3-oxazolidinyl) phosphinic chloride |
| EDC | 1-ethyl-3-(3-dimethylamino-propyl) carbodiimide hydrochloride |
| | Other |
| BOC-ON | 2-(tert-butylcarbonyloxyimino)-2-phenylacetonitrile |
| $(BOC)_2O$ $(BOC_2O$ or $Boc_2O)$ | di-t-butyl dicarbonate |
| $n\text{-}Bu_4N^+F^-$ | tetrabutyl ammonium fluoride |
| nBuLi (n-Buli) | n-butyllithium |
| (S)-CSA | (1S)-(+)-10-camphorsulfonic acid |
| DIEA or DIPEA | diisopropylethylamine |
| DMAP | dimethylaminopyridine |
| DME | dimethoxyethane |
| DMF | dimethylformamide |
| $Et_3N$ | triethylamine |
| EtOAc | ethyl acetate |
| h | hour(s) |
| IPA | 2-propanol |
| LDA | lithium diisopropylamide |
| L-PGA | (L)-pyroglutamic acid |
| TFA | trifluoroacetic acid |
| THF | tetrahydrofuran |
| TLC | thin layer chromatography |

DETAILED DESCRIPTION OF THE INVENTION

The instant invention provides a novel process for making intermediates of formulas I and II which are useful in the preparation of HIV protease inhibitors, and in particular those compounds disclosed in EPO541,168. The process for making intermediates of formula I

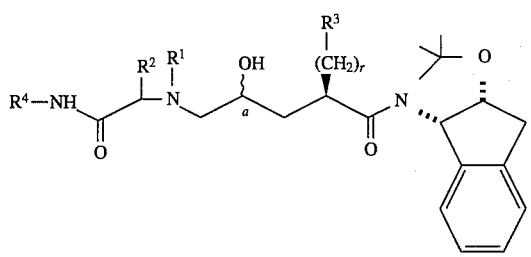

comprises the steps of:

(1) producing a compound of formula II

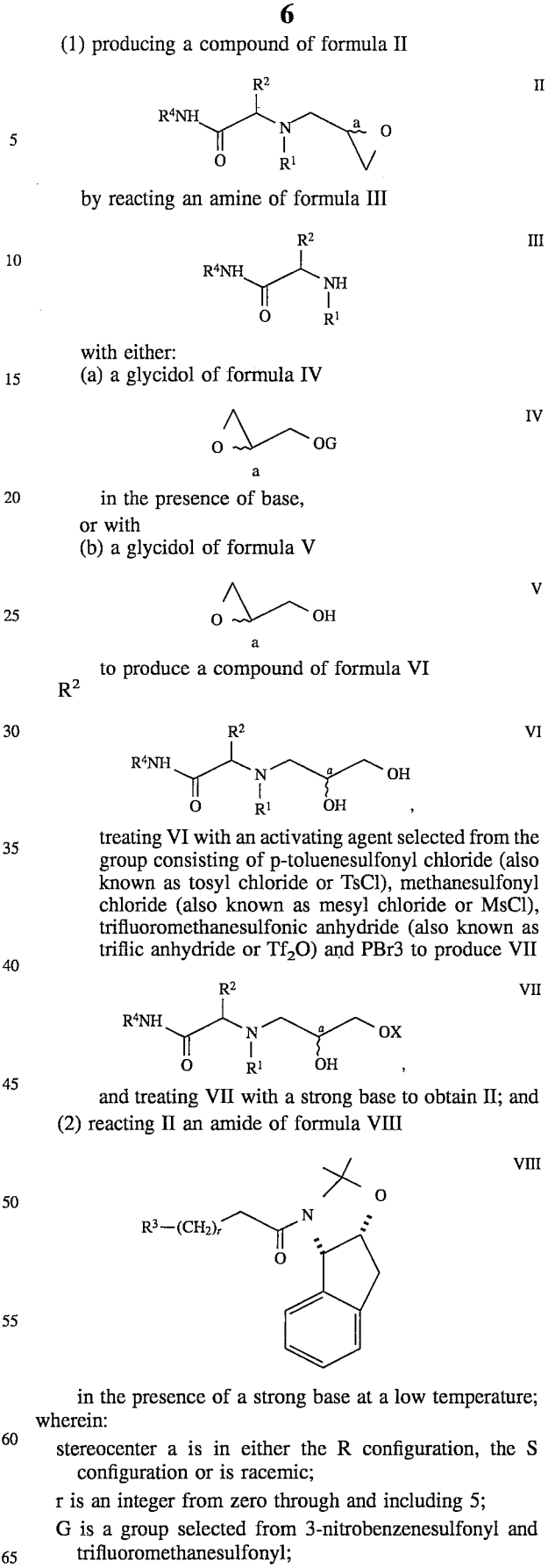

by reacting an amine of formula III with either:
(a) a glycidol of formula IV in the presence of base,
or with
(b) a glycidol of formula V to produce a compound of formula VI treating VI with an activating agent selected from the group consisting of p-toluenesulfonyl chloride (also known as tosyl chloride or TsCl), methanesulfonyl chloride (also known as mesyl chloride or MsCl), trifluoromethanesulfonic anhydride (also known as triflic anhydride or $Tf_2O$) and $PBr_3$ to produce VII and treating VII with a strong base to obtain II; and
(2) reacting II an amide of formula VIII in the presence of a strong base at a low temperature; wherein:
stereocenter a is in either the R configuration, the S configuration or is racemic;
r is an integer from zero through and including 5;
G is a group selected from 3-nitrobenzenesulfonyl and trifluoromethanesulfonyl;

X is a group selected from p-toluenesulfonyl, methanesulfonyl, and trifluoromethanesulfonyl;

$R^1$ and $R^2$ are independently selected at each occurrence from the group consisting of:
1) hydrogen,
2) —$C_{1-4}$ alkyl unsubstituted or substituted with one or more of
   a) hydroxy,
   b) $C_{1-3}$ alkoxy,
   c) aryl unsubstituted or substituted with one or more of $C_{1-4}$alkyl, hydroxy or aryl,
   d) —W-aryl or —W-benzyl, wherein W is —O—, or —S—,
   e) a 5–7 membered cycloalkyl group unsubstituted or substituted with one or more of
      i) hydroxy,
      ii) $C_{1-3}$ alkoxy, or
      iii) aryl,
   f) heterocycle unsubstituted or substituted with one or more of hydroxy, $C_{1-4}$alkyl, $C_{1-4}$alkyl substituted with hydroxy, or Boc,
   g) —NH—COO$C_{1-3}$alkyl,
   h) —NH—CO—$C_{1-3}$alkyl,
   i) —NH—SO$_2C_{1-3}$alkyl,
   j) —COOR, or
   k) —((CH$_2$)$_m$O)$_n$R, or
3) aryl, unsubstituted or substituted with one or more of
   a) halo,
   b) hydroxy,
   c) —NO$_2$ or —N(R)$_2$,
   d) $C_{1-4}$alkyl,
   e) $C_{1-3}$ alkoxy, unsubstituted or substituted with one or more of —OH or $C_{1-3}$ alkoxy,
   f) —COOR,
   g) —CON(R)$_2$,
   h) —CH$_2$N(R)$_2$,
   i) —CH$_2$NHCOR,
   j) —CN,
   k) —CF$_3$,
   L) —NHCOR,
   m) aryl $C_{1-3}$ alkoxy,
   n) aryl,
   o) —NRSO$_2$R,
   p) —OP(O)(OR$_x$)$_2$, or
   q) —$R^5$, as defined below; or $R^1$ and $R^2$ can be joined together with the nitrogen to which $R^1$ is attached and the carbon to which $R^2$ is attached to form a 3 to 10 membered monocyclic or bicyclic saturated ting system which consists of the nitrogen to which $R^1$ is attached and from 2 to 9 carbon atoms such as, for example,

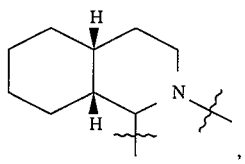

and is unsubstituted or substituted with one or more of:
1) hydroxy,
2) $C_{1-4}$ alkyl unsubstituted or substituted with one or more of
   a) halo,
   b) hydroxy,
   c) $C_{1-3}$ alkoxy,
   d) aryl,
   e) a 5–7 membered cycloalkyl group unsubstituted or substituted with one or more of
      i) hydroxy,
      ii) $C_{1-3}$ alkoxy, or
      iii) aryl, or
   f) heterocycle,
3) $C_{1-3}$ alkoxy,
4) —NH—COO$C_{1-3}$alkyl,
5) —NH—CO—$C_{1-3}$alkyl,
6) —NH—SO$_2C_{1-3}$alkyl,
7) heterocycle,
8) —W-aryl, or
9) —W—CO-aryl, wherein W is defined above; or $R^1$ and $R^2$ can be joined together with the nitrogen to which $R^1$ is attached and the carbon to which $R^2$ is attached to form a 3 to 10 membered monocyclic or bicyclic saturated ting system which consists of the nitrogen to which $R^1$ is attached, from 1 to 8 carbon atoms and one or more unsubstituted or substituted heteroatom selected from
1)

wherein V is absent or —CO—Q— or —SO$_2$—Q—, $R^1$ is defined as above for when $R^1$ is independent from and not joined to $R^2$, and wherein Q is absent or —O—, —NR—, or heterocycle optionally substituted with —$C_{1-4}$alkyl,
2)

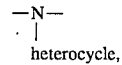

3)

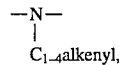

unsubstituted or substituted with aryl,
4)

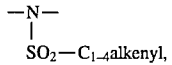

unsubstituted or substituted with aryl,
5) —S(O)$_p$—,
wherein p is zero, 1 or 2, or
6) —O—,
such as, for example,

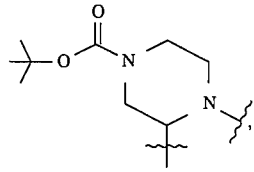

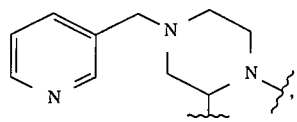

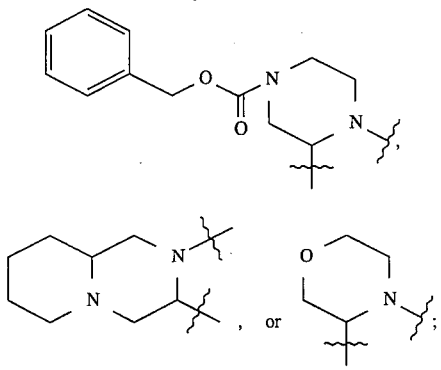

$R^3$ is selected from the group consisting of:
1) hydrogen,
2) —$C_{1-4}$ alkyl
3) $C_5$–$C_{10}$ cycloalkyl, optionally substituted with hydroxy,
4) $C_6$–$C_{10}$ aryl, unsubstituted or substituted with one or more of:
   a) halo,
   b) hydroxy,
   c) —$NO_2$ or —$N(R)_2$,
   d) $C_{1-4}$ alkyl,
   e) $C_{1-3}$ alkoxy, unsubstituted or substituted with one or more of —OH or $C_{1-3}$ alkoxy,
   f) —COOR,
   g) —$CON(R)_2$,
   h) —$CH_2 N(R)_2$,
   i) —$CH_2 NHCOR$,
   j) —CN,
   k) —$CF_3$,
   l) —NHCOR,
   m) aryl $C_{1-3}$ alkoxy,
   n) aryl,
   o) —$NRSO_2R$,
   p) —$OP(O)(OR_x)_2$, or
   q) —$R^5$, as defined below, or
5) monocyclic or bicyclic heterocycle containing from 1 to 3 heteroatoms chosen from the group consisting of N, O, and S, such as, for example, 2-pyridyl, 3-pyridyl, or 4-pyridyl, and which is unsubstituted or substituted with $R^5$ and optionally with one or more of
   a) halo,
   b) $C_{1-4}$ alkyl, or
   c) $C_{1-3}$ alkoxy;

m is 2, 3, 4 or 5;

n is zero, 1, 2 or 3;

R is hydrogen or $C_{1-4}$ alkyl;

$R_x$ is H or aryl;

$R^4$ is $C_{1-5}$ alkyl, straight or branched chain; and $R^5$ is
1) —W—$(CH_2)_m$—$NR^6R^7$ wherein W and m are defined above, and $R^6$ and $R^7$ are independently selected at each occurrence from:
   a) hydrogen,
   b) $C_{1-6}$ alkyl, unsubstituted or substituted with one or more of
      i) $C_{1-3}$ alkoxy,
      ii) —OH, or
      iii) —$N(R)_2$,
   c) aromatic heterocycle unsubstituted or substituted with one or more of
      i) $C_{1-4}$ alkyl, or
      ii) —$N(R)_2$,
   d) or $R^6$ and $R^7$ are joined together with the nitrogen to which they are attached to form a 5–7 member heterocycle, such as morpholino, containing up to two additional heteroatoms selected from —N(R), —O—, —S—, —S(O)— or —$S(O)_2$—, the heterocycle optionally substituted with $C_{1-4}$ alkyl,
2) —$(CH_2)_q$—$NR^6R^7$ wherein q is an integer from 1–5, and $R^6$ and $R^7$ are defined above, except that $R^6$ or $R^7$ are not H or unsubstituted $C_{1-6}$ alkyl, or
3) benzofuryl, indolyl, azacycloalkyl, azabicyclo $C_{7-11}$ cycloalkyl, or benzopiperidinyl, unsubstituted or substituted with $C_{1-4}$ alkyl.

Schemes 1 and 2 below illustrate this process. However, the instant process is not limited by any particular substituents employed in the schemes which are used for the purpose of illustration.

SCHEME 1

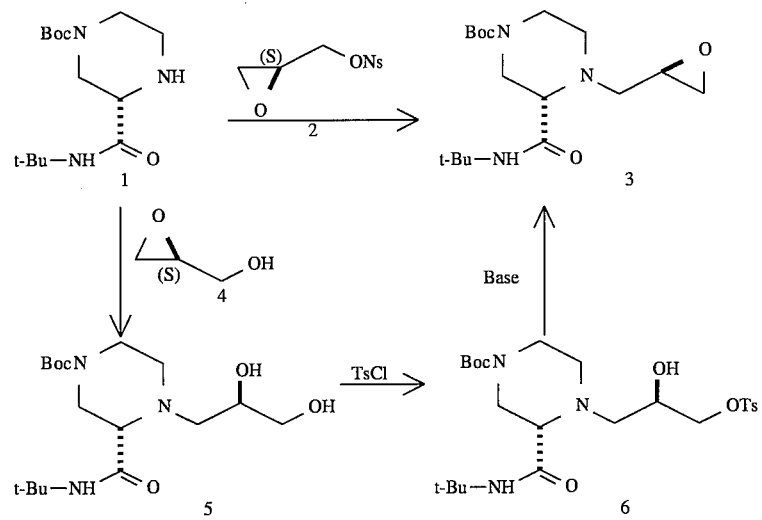

SCHEME 2

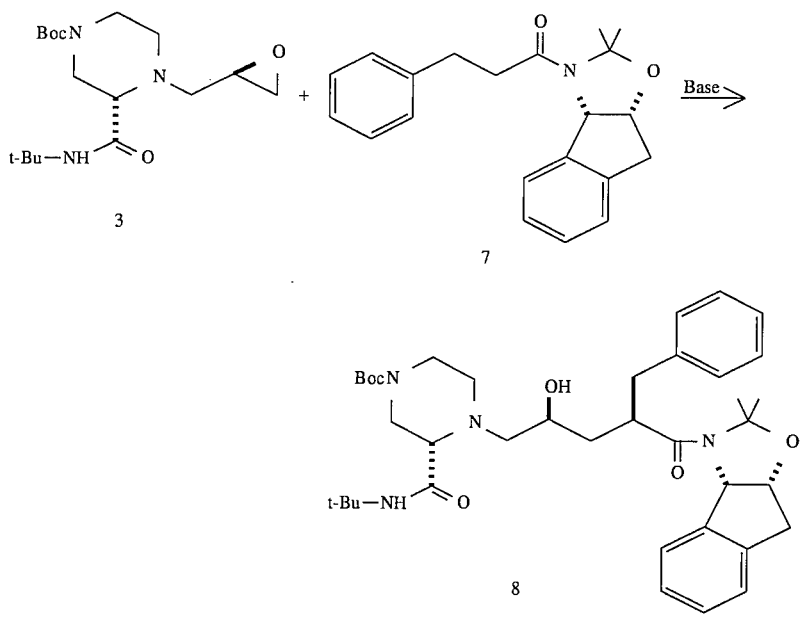

A suitable group may be used to activate glycidol IV, such as, e.g., 3-nitrobenzenesulfonyl or trifluoromethanesulfonyl, with 3-nitrobenzenesulfonyl being preferred. Any suitable polar solvent may be used for the reaction of III with IV such as e.g., dimethylformamide (DMF), N-methyl pyrrolidinone, acetone, butanone, acetonitrile, tert-butyl alcohol, tert-amyl alcohol, 2-propanol, N-ethyl pyrrolidinone, 1,1,3, 3-tetramethylurea, dimethylsulfoxide, 1,3-dimethyl-3,4,5,6-tetrahydro-2(1H)-pyrimidinone, tetramethylsulfone, tetrahydrofuran (THF), 1,4-dioxane, pyridine and water, and combinations thereof. The preferred polar solvents are DMF, N-methylpyrrolidinone, acetone, 2-butanone and acetonitrile, with DMF being most preferred. Any suitable base may be used for the reaction of III with IV, and such bases include, e.g., diisopropylethylamine (DIEA), potassium carbonate, sodium carbonate, sodium bicarbonate, triethylamine, pyridine, and dimethylaniline; DIEA and potassium carbonate are preferred, with DIEA being most preferred. Preferably, about 1:1 molar equivalents of III:IV are used in this reaction step. The reaction is preferably run at an elevated temperature, for example in the range of about 50° C. to 70° C., with about 60° C. to 65° C. being more preferred.

Glycidol V is reacted with amine III in a ratio of about 1–3 molar equivalents of V per one mole of III, with a molar equivalent ratio of about 1.5:1 of V:III being preferred, in a suitable solvent. Suitable solvents include, e.g. hydrocarbons, ethers such as di-ethyl ether, alcohols such as methanol, ethanol, or isopropanol, nitriles such as acetonitrile, and esters such as ethyl acetate or combinations thereof, with alcohols being preferred. The reaction may be run at a temperature between ambient temperature and the reflux temperature of the solvent used, with an elevated temperature preferred. Most preferably, the solvent is isopropanol and the reaction is run at about 85° C.

The hydroxy group of VI is activated to form VII using standard techniques known to those in the art. From about 1 to 3 molar equivalents of TsCl, MsCl, or $Tf_2O$ per molar equivalent of VI can be used for this purpose, with a ratio of about 1.5:1 molar equivalents of activating agent:VI preferred. X is preferably p-toluenesulfonyl, and therefore TsCl is preferred for this step. The reaction is preferably run at ambient temperature, i.e., about 25° C., but it can be run at a lower or higher temperature such as from −20° to 80° C. Any suitable solvent known to those skilled in the art may be used in this step, such as e.g., hydrocarbons, ethers, nitriles, esters, and amines such as pyridine or combinations thereof. Pyridine is most preferred as the solvent. It is preferable not to use an alcoholic solvent.

The activated intermediate VII is finally treated with a strong base preferably at room temperature to form II, although the reaction may be run at lower and higher temperatures as from 0° C. to the reflux temperature of the solvent used. Suitable strong bases include NaH, $KOC(CH_3)_3$, $KOC(CH_3)_2CH_2CH_3$, $NaOC(CH_3)_2CH_2 CH_3$, lithium diisopropylamide (LDA), n-butyllithium (n-BuLi), lithium bis(trimethylsilyl)amide or a similar strong base known in the art, and NaH is preferred. About 1 to 3 molar equivalents of base is generally used per molar equivalent of VII, with a ratio of 1.5:1 molar equivalents of base:VII being preferred. Any suitable solvents can be used in this step, such as, e.g., hydrocarbons, ethers, nitriles, and esters or combinations thereof, with THF being the preferred solvent. It is preferable not to use an alcoholic solvent.

Intermediates VIII and II are coupled using a strong base in an etherial solvent. The strong base must be a metal-containing base. The strong base may or may not be in an inert anhydrous organic solvent, such as, e.g., cyclic or acyclic hydrocarbons including hexane, pentane, cyclohexane, etc. Suitable strong bases include: n-butyllithium (n-BuLi), s-BuLi, t-BuLi, lithium diisopropylamide (LDA), lithium isopropylcyclohexylamide, lithium pyrrolidide, lithium tetramethylpiperidide, phenyllithium, isopropylmagnesium chloride, isobutylmagnesium chloride, and other similar strong bases known in the art. Preferred strong bases are n-BuLi, s-BuLi, and LDA, with n-BuLi being most preferred. About 1 to 2 molar equivalents of base can be used per molar equivalent of VIII; preferably, 1.05 to 1.2 molar equivalents and most preferably 1.15 molar equivalents of base are used per molar equivalent of VIII. The reaction of VIII with II can be done by combining VIII and II in one pot and then adding the strong base, or it can be done sequentially, i.e., by first treating amine VIII with base followed by addition of II.

The strong base effects metalation of the amide VIII at the position alpha to the carbonyl group to afford the reactive metal amide enolate which then effects ting opening of the epoxide II at the terminal position to afford compound I. A new center of asymmetry is created in the product isostere I at the 2-position.

The reaction is preferably rum at a low temperature, for example ranging between about –82° C. and 0° C. To effect metalation of the amide VIII, the temperature range is maintained more preferably between about –82° C. and 40° C. and most preferably between about –50° C. and –45° C. To effect the reaction of the metalated amide derivative of VIII and the glycidol derivative II to form I, the temperature range is maintained more preferably between about –50° C. and –10° C., and most preferably between about –30° C. to –20° C. for about 4–5 hours, although the length of the reaction may vary depending on the reaction scale and other factors known to those skilled in the art.

The etherial solvents are any solvents suitable for use in this coupling step including, e.g., THF, 1,2-dimethoxy-ethane, di-ethyl ether and methyl-t-butyl ether, with THF being preferred.

Activated glycidols of formula IV can be prepared by methods known in the art, such as described in, e.g., J. Klunder, et al., *J. Org. Chem.*, 1989, 54, 1295–1304 and references cited therein.

Compounds of formula VIII can be made according to standard procedures known to those skilled in the art, such as, e.g., the procedure described in Example 1, using the appropriate starting materials.

Protecting groups such as nitrogen protecting groups may be used where appropriate in the practice of this invention. For example, the 4 position nitrogen of 2-t-butylcarboxamide piperazine may be protected with a group such as BOC, CBZ, benzyl, 4-methoxybenzyl, 2,4-dimethoxybenzyl, trifluoroacetamide, trialkylsilyl, or other groups known in the art.

End-product HIV protease inhibitors are made from compounds of formula I by removing any remaining protecting groups present according to deprotection methods well known to those skilled in the art. For example, the ketal protecting group can be removed by treating I with acid in the presence of methanol, or by aqueous acid or by 1N NCl in THF, to produce the final HIV protease inhibitor products. Compounds of formula I may also be further substituted by methods known in the art.

In one embodiment of this invention, stereocenter a has the S configuration; r is 1; G is 3-nitrobenzenesulfonyl; X is p-toluenesulfonyl; $R^1$ and $R^2$ are joined together to form a cyclic structure selected from the group consisting of:

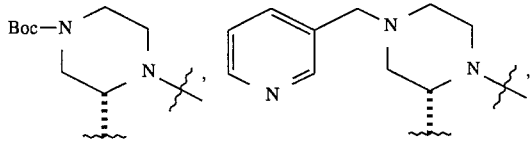

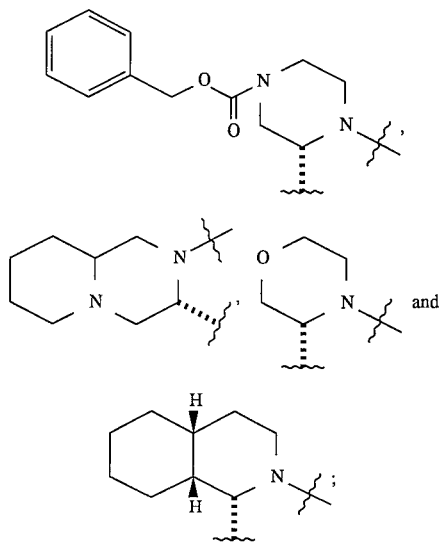

$R^3$ is selected from phenyl,

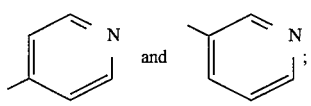

and $R^4$ is tert-butyl.

Within this embodiment is the preferred species of formula II which is the intermediate compound of formula II-a

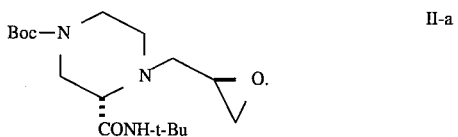

II-a

Also within this embodiment are the preferred species of formula I, which are the intermediate compounds of formulas I-a and I-b

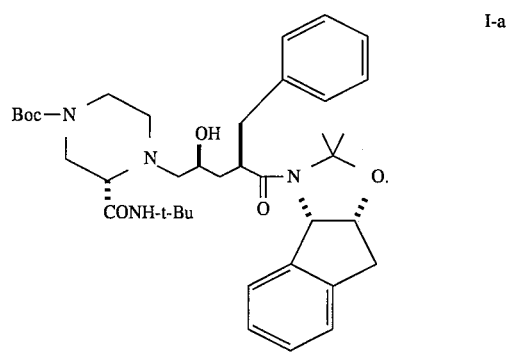

I-a

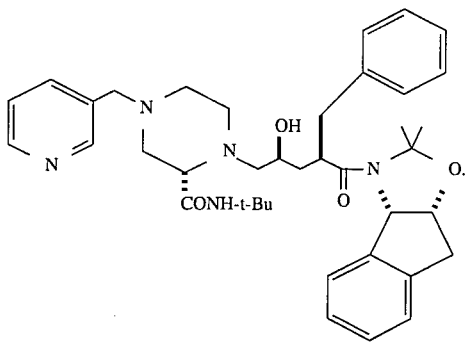

Compound I-b can be made by directly coupling the 4N-methylpyridyl derivative of II-a with the appropriate species of formula VIII. Preferably, the final product L-735, 524 is made by deprotection and picolylation of I-a, as exemplified in Examples 10–11.

Another embodiment of this invention involves the preparation of the chiral intermediate (S)-2-tert-butylcarboxamide-4-tert-butoxycarbonylpiperazine 1. Compound 1 is obtained by treatment of a salt form of (S)-2-tert-butylcarboxamidepiperazine with base followed by $Boc_2O$. Nitrogen protecting groups other than Boc, such as CBZ, benzyl, etc., may also be used.

The formation and resolution of the salt form of (S)-2-tert-butylcarboxamidepiperazine is accomplished by a novel process comprising the steps of:

(a) contacting a solution of (S)(R)-2-tert-butylcarboxamide-piperazine with an acid in an aqueous-organic solvent mixture, wherein the acid is selected from the group consisting of (+) or (−) tartaric acid, (+) or (−) mandelic acid, (+) or (−) dibenzoyltartaric acid, D or L-pyroglutamic acid (also known as (+) or (−) 2-pyrrolidine-5-carboxylic acid), (+) or (−) di-O,O'-p-toluyltartaric acid, (+) or (−)malic acid, (+) or (−)-10-camphorsulfonic acid (+) or (−)-3-bromo-10-camphorsulfonic acid, and (+) or (−)-3-chloro-10-camphorsulfonic acid;

(b) heating the mixture to dissolve any solid that forms;

(c) cooling the mixture;

(d) separating the precipitated crystals from the mother liquor; and (e) if the mother liquor is predominantly comprised of the (S)-antipode, removing the solvent therefrom.

The organic solvents suitable for the resolution process include, e.g., water miscible solvents such as THF, 1,4-dioxane, acetonitrile, DMF, 1-methyl-2-pyrrolidinone, dimethoxyethane, ethyl acetate, $C_{1-4}$ alcohols such as methanol, ethanol, 1-propanol, isopropanol, n-butanol, and sec-butanol, and combinations thereof. Preferably, the organic solvent is a $C_{1-4}$ alcohol, or $C_{1-4}$ alcoholacetonitrile mixture, and more preferably, the alcohol is selected from 1-propanol and ethanol. Although the amount of water in the aqueous-organic solvent mixture may be varied, preferably the volume percent of water in the mixture is 15 percent or less, and more preferably 5 percent or less.

About 1 to 3 molar equivalents of the acid per molar equivalent of the racemic piperazine derivative are advantageously used in this procedure, and it is preferable to form the bis-acid salt. (1S)-(+)-10-Camphorsulfonic acid and (L)-pyroglutamic acid are the preferred acids, and (L)-pyroglutamic acid is most preferred.

The temperatures at which steps (b) and (c) are performed may be varied according to techniques known to those skilled in the art. Generally, a temperature sufficient to dissolve any solids is all that is needed for step (b), and may, e.g., be in the range of about 70° C. to the reflux temperature of the solvent used. The heated solution should be allowed to cool slowly, preferably of its own accord, down to ambient temperature, and may be further cooled to about 20°–23° C. for step (c). Optionally, the solution may be seeded with the appropriate salt of either (S) or (R)-2-tert-butylcarboxamidepiperazine to promote crystallization.

After separating the crystalline precipitate from the mother liquor, it can be determined whether the precipitate contains predominantly the R or the S-antipode by standard techniques known in the art, such as a chiral HPLC assay. "Predominantly" is intended to mean an enantiomeric excess (ee) of 90% or greater. The S-antipode can then be recovered from the precipitate or the mother liquor accordingly. For example, when the CSA salt is prepared, the S-antipode crystallizes out of solution; however, when the L-PGA salt is formed, the S-antipode remains in the mother liquor and the R-antipode crystallizes out.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carder and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention.

When any variable (e.g., aryl, heterocycle, R, $R^1$, $R^2$, n, X, etc.) occurs more than one time in any constituent or in formulas I-VIII, its definition on each occurrence is independent of its definition at every other occurrence. Also, combinations of substituents and/or variables are permissible only if such combinations result in stable compounds.

17

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl); "alkoxy" represents an alkyl group of indicated number of carbon atoms attached through an oxygen bridge; and "cycloalkyl" is intended to include saturated ring groups, such as cyclopropyl, cyclobutyl, cyclopentyl, cyclohexyl (Cyh) and cycloheptyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Alkynyl" is intended to include hydrocarbon groups of either a straight or branched configuration with one or more carbon-carbon triple bonds which may occur in any stable point along the chain, such as ethynyl, propynyl, butynyl, pentynyl, and the like. "Halo ", as used herein, means fluoro, chloro, bromo and iodo. As used herein, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ting may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

Representative experimental procedures utilizing the novel process are detailed below. These procedures are exemplary only and should not be construed as being limitations on the novel process of this invention.

EXAMPLE 1

Preparation of Amide 7

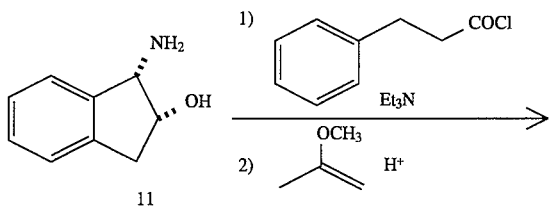

18

-continued

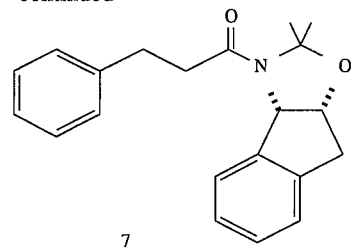

7

A solution of (−)-cis-1-aminoindan-2-ol 11 (884 g, 5.93 mol) in 17.8 L of dry THF (KF=55 mg/mL) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature was maintained between 14°–24° C. with an ice-water cooling batch. After the addition, the mixture was aged at 18° to 20° C. for 30 minutes and checked by HPLC analysis for the disappearance of 11.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500×dilution. Approximate retention times:

| retention time (min.) | identity |
| --- | --- |
| 4.1 | hydroxy amide |
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26"of Hg) at 40° C. to afford 1.65 kg of acetonide 7 (86.4%, 98 area % by HPLC), $^1H$ NMR (300.13 MHz, $CDCl_3$, major rotamer) δ7.36–7.14 (m, 9H), 5.03 (d, J=4.4, 1H), 4.66 (m, 1H) 3.15 (m, 2H), 3.06 (br s, 2H), 2.97 (m, 2H), 1.62 (s, 3H), 1.37 (s, 3H); $^{13}C$ NMR (75.5 MHz, $CDCl_3$, major rotamer) $δ_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1. Anal. Calcd for $C_{21}H_{23}NO_2$: C, 78.47; H, 7.21; N, 4.36. Found: C, 78.65; H, 7.24; N, 4.40.

EXAMPLE 2

Pyrazine-2-tert-butyl carboxamide 13

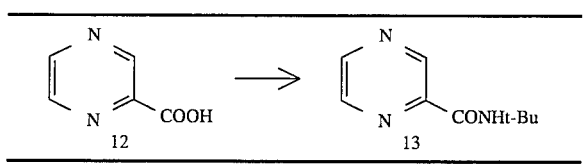

| | |
|---|---|
| 2-Pyrazinecarboxylic acid (12) | 3.35 kg (27 mol) |
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 12 was suspended in 27 L of EtOAc and 120 mL of DMF in a 72 L 3-neck flask with mechanical stirring under N2 and the suspension was cooled to 2° C. The oxalyl chloride was added, maintaining the temperature between 5 and 8° C.

The addition was completed in 5 h. During the exothermic addition CO and $CO_2$ were evolved. The HCl that was formed remained largely in solution. A precipitate was present which is probably the HCl salt of the pyrazine acid chloride. Assay of the acid chloride formation was carried out by quenching an anhydrous sample of the reaction with t-butylamine. At completion <0.7% of acid 12 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 12=10.7 min, amide 13=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Hok and the cake was washed with 4 L of EtOAc. Carbon treatment efficiently removed some purple color in the product.

The EtOAc solution of 13 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 13 was stable to reflux at atmospheric pressure for several days.

Evaporation of an aliquot gave a tan solid m.p 87°–88° C.; $^{13}C$ NMR (75 MHz, $CDCl_3$, ppm) 161.8, 146.8, 145.0, 143.8, 142.1, 51.0, 28.5.

EXAMPLE 3 rac-2-tert-Butyl-carboxamide-piperazine 14

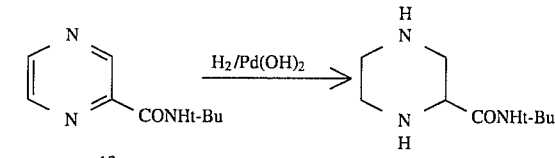

Materials

Pyrazine-2-tert-butylcarboxamide 13 (2.4 kg, 13.4 mol) in 1-Propanol solution 12 L 20% $Pd(OH)_2/C$ 16 wt. % water 144 g.

The pyrazine-2-tert-butylcarboxamide 13/1-propanol solution was placed into the 5 gal autoclave. The catalyst was added and the mixture was hydrogenated at 65° C. at 40 psi (3 atm) of $H_2$.

After 24 h. the reaction had taken up the theoretical amount of hydrogen and GC indicated <1% of 13. The mixture was cooled, purged with $N_2$ and the catalyst was removed by filtration through Solka Floe. The catalyst was washed with 2 L of warm 1-propanol.

It was found that the use of warm 1-propanol during washing of the filter cake improved filtration and lowered the losses of product on the filter cake.

The reaction was monitored by GC (gas chromatography): 30 m Megabore column, from 100° C. to 160° C. at 10° C./min, hold 5 min, then at 10° C./min to 250° C., retention times: 13=7.0 min, 14=9.4 min. The reaction could also be monitored by TLC (thin layer chromatography) with EtOAc/MeOH (50:50) as solvent and Ninhydrin as developing agent.

Evaporation of an aliquot indicated that the yield over amidation and hydrogenation is 88% and that the concentration of 14 is 133 g/L.

Evaporation of an aliquot gave 14 as a white solid m.p. 150°–151° C.; $^{13}C$ NMR (75 MHz, $D_2O$, ppm) 173.5, 59.8, 52.0, 48.7, 45.0, 44.8, 28.7.

EXAMPLE 4

(S)-2-tert-Butyl-carboxamide-piperazine bis (S)-Camphorsulfonic acid salt (S)-15

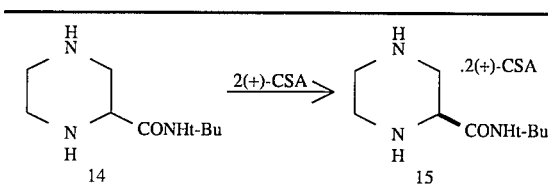

Materials

| | |
|---|---|
| rac-2-tert-Butyl-carboxamide-piperazine 14 in 1-Propanol Solution | 4.10 kg (22.12 mol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 14 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 14 was 341 g/L The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 14: 2.5 min.

Acetonitrile (39 L) and water (2.4 L) were added to give a clear, slightly brown solution.

Determination of the water content by KF titration and $CH_3CN$/1-propanol ratio by $^1H$ NMR integration showed that the $CH_3CN$/1-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN$ /1-propanol/$H_2O$ 26/8/1.6 solvent mixture. It was dried at 35° C. in the vacuum oven with $N_2$ bleed to give 5.6 Kg (39%) of 15 as a white crystalline solid m.p 288°–290° C. (with decomp.) $[\alpha]D^{25}=18.9°$ (c=0.37, $H_2O$). $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The enantiomeric excess (ee) of the material was 95% according to the following chiral HPLC assay: an aliquot of 15 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 5

(S)-2-tert-Butylcarboxamide-4-tert-butoxycarbonyl-piperazine 1 from salt 15

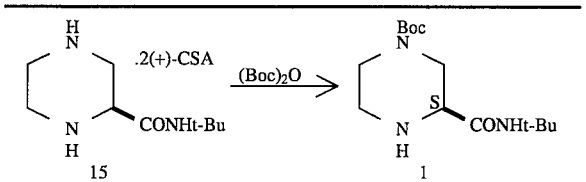

Materials

| | |
|---|---|
| (S)-2-tert-Butyl-carboxamide-piperazine Bis(S)-(+)-CSA salt 15, 95% ee | 5.54 Kg (8.53 mol) |
| Di-tert-butyl dicarbonate Lacamas | 1.86 Kg (8.53 mol) |
| $Et_3N$ Aldrich | 5.95 L (42.6 mol) |
| EtOH Punctilious 200 proof | 55 L |
| EtOAc | 2 L |

To the (S)-CSA salt 22 in a 100 L 3-neck flask with an addition funnel under $N_2$ was added EtOH, followed by triethylamine at 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC: 25 cm Dupont Zorbax $RXC_8$ column with 1 mL/min flow and detection at 228 nm, isocratic (50/50) $CH_3CN/0.1$ M $KH_2PO_4$ adjusted to pH=6.8 with NaOH. Retention time of 1=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22 ° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 1 as a slightly tan powder. $[\alpha]D^{25=22.0°}$ (c=0.20, MeOH), m.p 107 ° C.; $^{13}C$ NMR (75 MHz, $CDCl_3$, ppm) 170.1, 154.5, 79.8, 58.7, 50.6, 46.6, 43.6, 43.4, 28.6, 28.3.

EXAMPLE 6

(S)-2-tert-Butyl-carboxamide-piperazine bis (L)-Pyroglutamic acid 16

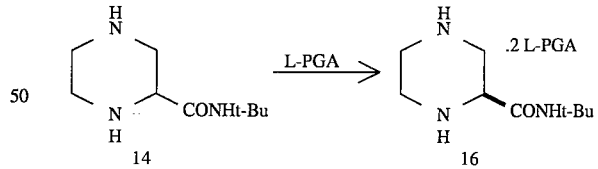

Materials

| | |
|---|---|
| rac-2-tert-butyl-carboxamide-piperazine 14 in 1-propanol solution | (0.11 mol) 155 ml, assay = 21.1 g |
| L-pyroglutamic acid | 28 g, (0.21 mol) |
| Water | 5 ml |

The solution of racemic-2-tert-butyl-carboxamide-piperazine 14 in 1-propanol was charged to a 500 ml round bottom flask with a reflux condenser, mechanical stirrer and a nitrogen inlet. Water was added along with L-pyroglutamic acid and the resulting slurry was heated to reflux. The homogeneous yellow solution was cooled to 50° C. and seeded with the bis—(L)-PGA salt of the R amine (50 mgs). Solids began forming immediately. The solution was further cooled to 25° C. and aged for 16 hours. The solids were filtered at 22° C., and the filter cake was washed with 35 ml cold 1-propanol/1% water. The filter cake was dried at 35° C. in the vacuum oven with $N_2$ bleed to give 23.74 gms (48%) of (R)-2-tert-butyl-carboxamide-piperazine bis-(L)-pyroglutamic acid. The ee of the material was 98% according to the chiral HPLC assay described previously. The yellow mother liquors contained 22.6 gms (46%) of (S)-2-tert-butyl-carboxamide-piperazine bis (L)-pyroglutamic acid salt 16 and the ee was 95% according to the chiral HPLC assay. The mother liquors were evaporated and used directly in the protection step.

(S)-2-tert-butylcarboxamide-4-tert-butoxycarbonyl-piperazine 1 from (S)-2-tert-butyl-carboxamide-piperazine bis (L)-pyroglutamic acid salt 16

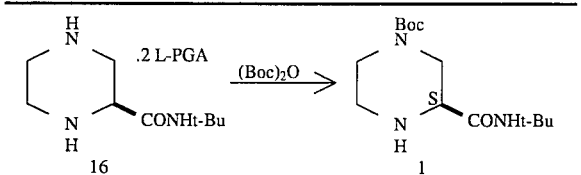

Materials

| | |
|---|---|
| (S)-2-tert-butyl-carboxamide-piperazine Bis(L)-pyroglutamic acid salt, 95% ee | 22.6 g (50.1 mmol) |
| Di-tert-butyl dicarbonate | 11.1 g (50.1 mmol) |
| $Et_3N$ | 35.5 mL (0.254 mol) |
| 1-Propanol | 226 ml |
| EtOAc | 24 ml |

To (S)-2-tert-butyl-carboxamide-piperazine bis (L)-pyroglutamic acid salt in a 500 ml 3-neck flask with addition funnel under $N_2$ was added 1-propanol. The gummy yellow solid dissolved readily on the addition of the $Et_3N$. A solution of $Boc_2O$ in EtOAc was added over 2 h at 22° C. The reaction mixture was aged for 1 h after completion of the addition.

The reaction could be monitored by HPLC (high performance liquid chromatography) and TLC using the same procedures as for the conversion of 15 to 1

The solution was then concentrated and solvent switched to ethyl acetate (200 ml). The reaction mixture was washed with 50 ml of 7% aqueous $Na_2CO_3$ solution, 2×30 ml water and dried ($Na_2SO_4$) and filtered. The EtOAc solution was concentrated and solvent switched to cyclohexane (60 ml). EtOAc (1 mL) was added and the mixture was heated to reflux to dissolve all solids. The mixture was cooled and seeded (50 mg) at 52° C. The slurry was cooled to 22° C. over 2 h and the product was isolated by filtration after a 1 h age at 22 ° C. The filter cake was washed with 8 ml of cyclohexane and dried in the vacuum oven at 35° C. under $N_2$ bleed to give 10.8 gms (74%, >99.9 area % by HPLC analysis, R-isomer below level of detection) of 1 as an off white powder.

EXAMPLE 7

1-((R)-2',3'-Epoxypropyl)-(S)-2-tert-butylcarboxamide-4-tert-butoxycarbonyl-piperazine 3

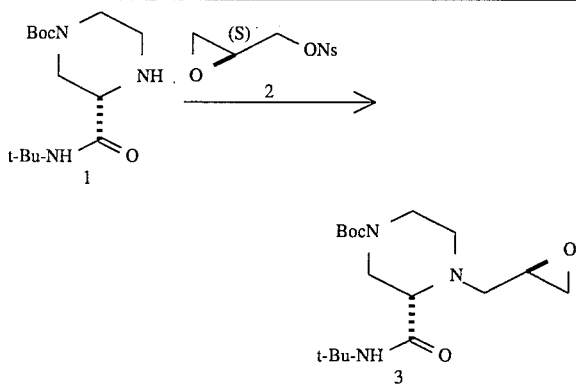

Materials

| | |
|---|---|
| (S)-2-tert-butylcarboxamide-4-tert-butoxycarbonyl-piperazine 1 | 11.0 g (38.4 mmol) |
| (2S)-(+)-Glycidyl-3-nitrobenzenesulfonate | 9.96 g (38.4 mmol) |
| Diisopropylethylamine | 5.5 mL (42.2 mmol) |
| DMF | 38 mL |

Piperazine 1 and (2S)-(+)-Glycidyl-3-nitrobenzenesulfonate 2 were dissolved in a 250 mL flask with magnetic stirring under $N_2$ in DMF and DIEA. The resulting homogenous solution was heated to 60°–62° C. for 9 h.

TLC (100% EtOAc as eluent, Ninhydrin stain) indicated complete consumption of piperazine 1.

The reaction was quenched by the addition of 30 mL of a 5% aqueous $NaHCO_3$ solution. The reaction mixture was extracted with 400 mL of isopropyl acetate. The organic phase was washed with water (3×50 mL) and brine (1×50 mL), dried ($Na_2SO_4$) and evaporated to give a yellow oil. Flash chromatography (4 cm×20 cm column, $SiO_2$, gradient elution with 30:70 EtOAc:hexanes to 60:40 EtOAc:hexanes) and evaporation of the product containing fractions gave 9.24 g (71% yield) of 3 as an oil:.$[\alpha]D^{25}=-17.7°$ (c=0.12, MeOH); $^{13}C$ NMR (100 MHz, $CDCl_3$, $-25°$ C., ppm of major rotamer) 170.0, 154.1, 80.2, 66.7, 56.3, 51.7, 50.8, 50.2, 47.0, 44.0, 41.9, 28.3, 28.1.

EXAMPLE 8

Preparation of Epoxide 3 from Piperazine 1 and (S)-Glycidol 4

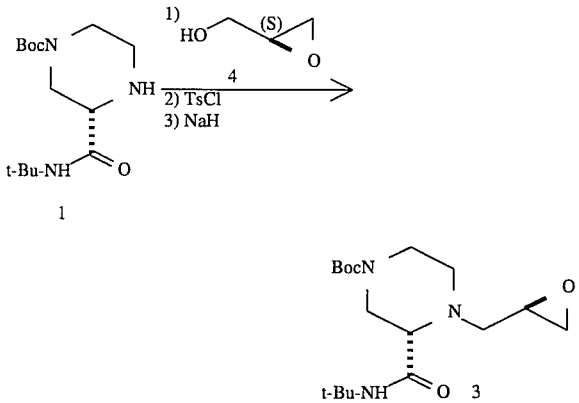

The piperazine 1 (2.00 g, 7.00 mmol) and (S)-glycidol 4 (930 μL, 14.0 mmol) were heated at reflux in 19 mL of isopropanol for 17 h, then the mixture was partitioned with 100 mL of ethyl acetate and 50 mL of water. The layers were separated, and the ethyl acetate layer was washed with saturated sodium chloride, dried with MgSO$_4$, and concentrated to 2.4 g of a gum. A portion of the gum (241 mg) was treated with 2 mL of pyridine and p-toluenesulfonyl chloride (130 mg, 0.68 mmol) overnight, then it was concentrated to an oil. The oil was partitioned with 25 mL of ethyl acetate and 10 mL of water. The ethyl acetate layer was washed with brine, dried (MgSO4) and concentrated to an oil. The crude oil was dissolved in 2 mL of THF and treated with 100 mg of 60% NaH dispersion in oil. After 1 h, the mixture was partitioned with ethyl acetate (50 mL), and 10 mL of water. The ethyl acetate layer was dried with MgSO$_4$ and concentrated to afford the desired epoxide 3 (see previous experimental for spectral data).

EXAMPLE 9

Preparation of Coupled Product 8 from Amide 7 and Epoxide 3

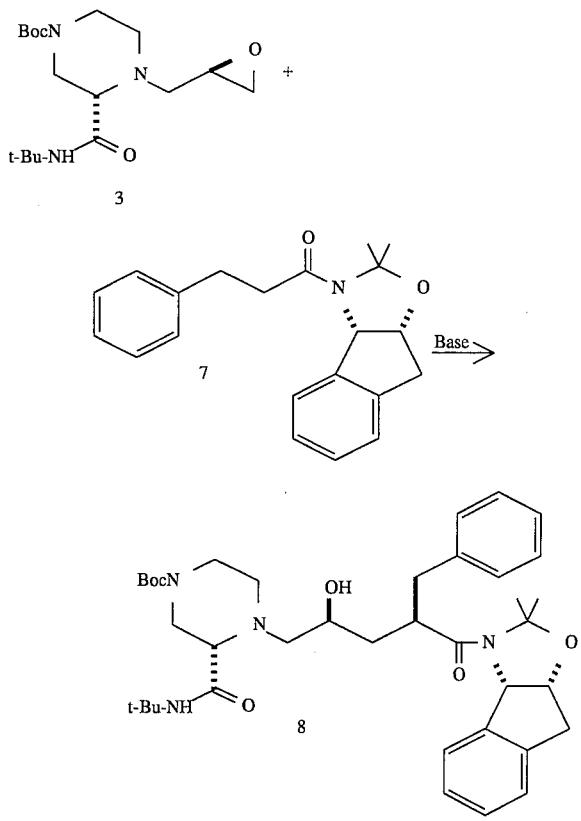

A solution of acetonide 7 (216 mg, 0.67 mmol) and N-Boc-piperazine epoxide 3 (229 g, 0.67 mmol, 1.0 equiv.) in 3.5 mL of THF (KF=22 μg/mL).(KF stands for Karl Fisher titration for water) in a 100 mL round bottom flask, equipped with a thermocouple, magnetic stirrer, and under nitrogen atmosphere, was cooled to −78° C. Then, n-butyllithium in hexanes solution (0.9 mL, 1.6M, 2.1 equiv.) was added, while keeping the internal temperature between −78° C. to −73° C. The reaction mixture was stirred at −76° C. for 1 h and then allowed to warm to −25° C. over 1 h. The mixture was stirred between −25 to −22° C. for 2.5 h. Then, the reaction mixture was quenched with DI water (5 mL) at −15° C. and partitioned with ethyl acetate (20 mL). The mixture was agitated and the layers were separated. The ethyl acetate extract was washed with saturated NaCl (10 mL) and concentrated under reduced pressure (28" of Hg) to afford crude product which was chromatographed on a silica gel column with ethyl acetate/hexane (3:2) to give the coupled product 8 (84 mg, 20%) as a pale yellow syrup: $^{13}$C NMR (CDCl$_3$, 75.4 MHz) δ172.6, 170.2, 154.6, 140.8, 140.4, 139.6, 129.5, 128.8, 128.1,127.2, 126.8, 125.6, 124.1, 96.7, 80.4, 79.2, 65.9, 65.8, 62.2, 51.3, 50.1, 45.3, 43.5, 39.5, 39.1, 36.2, 28.8, 28.4, 26.5, 24.2.

EXAMPLE 10

Preparation of penultimate 9

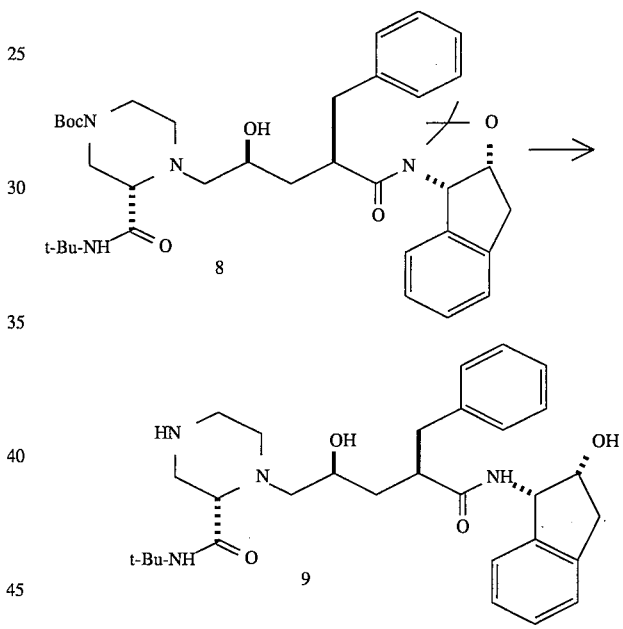

To a solution of compound 8 (5.79 g. 8.73 mmol) in 25.5 mL isopropanol at 0° C. was added 20 ml of 6N aqueous HCl, then 15 minutes later 10 mL of concentrated NCl was added. After 1 hour, the mixture was warmed to 20° C. and aged for 4 hours. The mixture was then cooled to 0° C., and the pH was adjusted to 12.5 with 13 mL of 50% aqueous NaOH, while keeping the temperature <29° C. The mixture was extracted with 2×80 mL of EtOAc, and the extracts were dried with MgSO$_4$ and concentrated to afford 5.46 g of the product 9 as a colorless foam: $^{13}$C NMR (75.4 MHz, CDCl$_3$) δ175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 11

Preparation of L-735,524-monohydrate

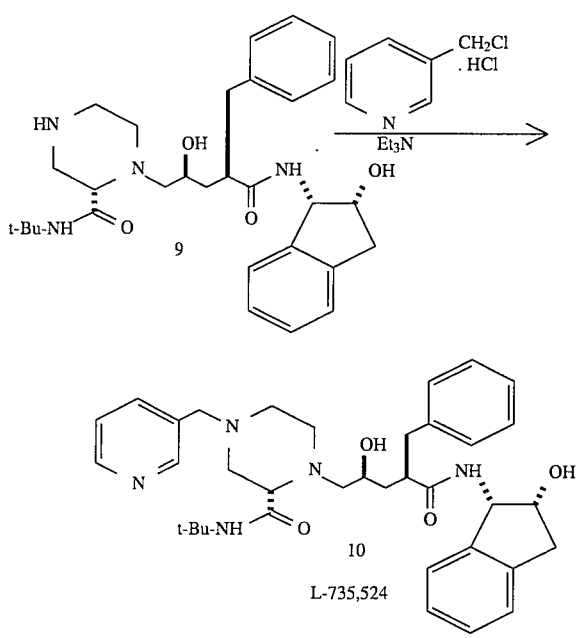

To the solution of 9 in EtOAc (10.5 L, KF=10 mg/mL) from the previous step was charged with 20 L of sieve dried DMF (KF <30 mg/L) and the mixture was heated with a steam bath under vacuum of 30" of Hg to distill off mainly water and/or any residual isopropanol or ethyl acetate solvent. The final concentrate volume was 13.5 L CKF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68 ° C.

The progress of the reaction was followed by HPLC analysis using the same conditions as the previous step. Approximate retention times:

| Retention time (min) | Identity |
| --- | --- |
| 2.7 | DMF |
| 4.2 | 3-picolyl chloride |
| 4.8 | L-735,524 |
| 9.1 | penultimate 9 |

The mixture was aged at 68° C. until the residual penultimate compound 9 was <0.3 area % by HPLC analysis. HPLC conditions: 25 cm Dupont $C_8$—RX column, 60:40 acetonitrile/10 mM ($KH_2PO_4/K_2HPO_4$), 1.0 ml/min, detection=220 nm.

The mixture was stirred at 68 ° C. for 4 h, then cooled to 25° C. and partitioned with ethyl acetate (80 L) and a mixture of 24 L of saturated aqueous $NaHCO_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with L-735,524 monohydrate. The mixture was cooled to 4° C. and filtered to collect the product. The product was washed with cold ethyl acetate (2×3 L), and dried at house vacuum at 25° C. to afford 2905 g (70.7 %) of L-735,524 as a white solid.

EXAMPLE 12

Kinetic Resolution of (S/R)-2-tert-Butylcarboxamide-4-tert-butoxycarbonyl-piperazine 17 to 1

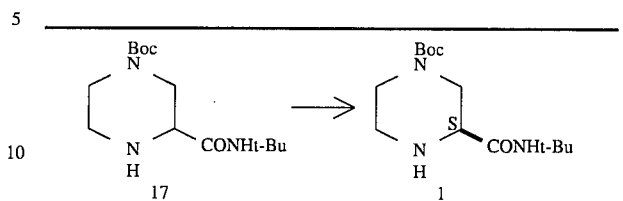

Materials

| | |
| --- | --- |
| Crude (S/R)-2-tert-Butylcarboxamide-4-tert-butoxycarbonyl-piperazine 17 | 1.40 g |
| (S)-2-tert-Butylcarboxamide-4-tert-butoxycarbonyl-piperazine 1 (>99.5% ee) | 4 × 0.14 g |
| Methylcyclohexane with 2% (vol/vol) EtOAc | 14 mL |

The crude, gummy 17 is dissolved in 14 mL of the solvent mixture by heating to 90° C. The solution is allowed to cool, and at 10° C. intervals the solution is seeded with 0.14 g of 1 (>99.5% ee). At 55° C. the fourth 0.14 g batch of seed does not dissolve any more and on further slow cooling to room temperature a white crystalline mass forms. The reaction mixture is filtered, washed with 3 mL of the methylcyclohexane/EtOAc solvent mixture and dried in the vacuum oven under $N_2$ bleed to give 0.95 g of a white solid. Determination of the enantiomeric purity with a Chiracell AS column shows 93%ee.

EXAMPLE 13

Preparation of trans-3-(4-pyridyl)acrylic acid

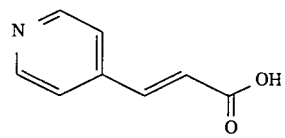

To a solution of 4-pyridine carboxaldehyde (36.7 mL, 0.384 mol) and malonic acid (40 g, 0.384 mol) in 31 mL of pyridine was added piperidine (0.12 mL) and the mixture was warmed to 100° C. Caution: large volumes of $CO_2$ evolved. After 0.5 h, the reaction was cooled to room temperature (RT) and the solution solidified. This was triturated with 240 mL of water and filtered, and washed with 2×50 mL portions of water. The solid was dried overnight at 42° C. under vacuum (10 mm Hg) to provide 37.1 g of a white solid; mp 295°–297° C.

EXAMPLE 14

Preparation of N-(2(R)-hydroxy-1(S)-indanyl)-trans-3-(4-pyridyl)acrylamide

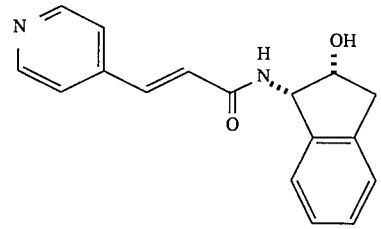

To a suspension of trans-3-(4-pyridyl)acrylic acid (10.0 g, 0.067 mol) in 500 mL of THF was added triethylamine (10.29 mL, 0.0738 mol) and the solution was cooled to 0° C. Trimethylacetyl chloride (8.68 mL, 0.0704 mol) was added and the reaction stirred for 0.5 h. 2(R)-hydroxy-1(S)-indane (10.0 g, 0.067 mol) dissolved in 260 mL of THF was added via cannula. After 2 h the reaction was warmed to RT and stirred an additional 15 h. The solvent was removed in vacuo and the resulting solid was triturated with cold ethyl acetate (150 mL) and filtered. This was dried overnight under vacuum (0.5 mm of Hg) to provide 18.58 of a white solid; mp 205°–207° C.

EXAMPLE 15

Preparation of N-(1,2-N,O-isopropylidenen-2(R)-hydroxy-1(S)-indanyl)-trans-3-(4-pyridyl)acrylamide

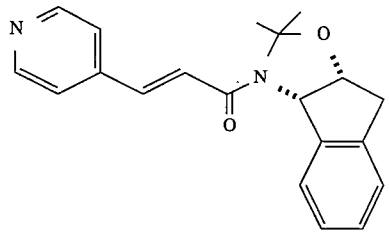

To a suspension of N-(2(R)-hydroxy-1(S)-indanyl)-trans-3-(4-pyridyl) acrylamide (18.58, 0.066 mol) in 700 mL of methylene chloride was added dimethoxypropane (49.0 mL, 0.402 mol) followed by (±) camphor sulphonic acid (46.8 g, 0.201 mol). After 20 minutes the reaction became homogeneous. The reaction mixture stirred for 3 h and was washed with saturated NaHCO$_3$ (2×150 mL). The aqueous layer was extracted with methylene chloride (3×200 mL) and the combined organic layer was dried over MgSO$_4$, filtered and concentrated to an oil. Purification by flash column chromatography (100×150 mm column of silica gel; gradient elution 1:30:69, 2:30:68, 3:30:67, 5:30:65 MeOH:CHCl$_3$ saturated with NH$_3$: CH$_2$ Cl$_2$) provided 16.0 g of a white foam. (Rf 0.46 in 5:30:65 MeOH:CNCl$_3$ saturated with NH$_3$: CH$_2$ Cl$_2$)

EXAMPLE 16

Preparation of N-(1,2-N,O-isopropylidenen-2(R)-hydroxy-1(S)-indanyl)-3-(4-pyridyl)propylamide

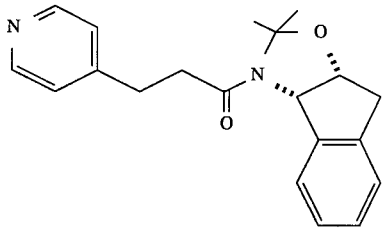

To N-(1,2-N,O-isopropylidenen-2(R)-hydroxy-1(S)-indanyl)-trans-3-(4-pyridyl)acrylamide (16.0 g, 0.0499 mol) dissolved in ethanol (200 mL) and THF (200 mL) was added 14.0 g Pd(OH)$_2$ on carbon (20% by weight). The flask was then charged with H$_2$ and stirred 9 h. The solution was purged with Ar, filtered through a plug of celite and washed with ethanol (100 mL). The solvent was removed in vacuo and the product was purified via flash column chromatography (100×150 mm column of silica gel; gradient elution 1:30:69, 2:30:68, 3:30:67, 5:30:65 MeOH:CHCl$_3$ saturated with NH$_3$: CH$_2$Cl$_2$) which provided 13.8 g of a white foam. (Rf 0.5 in 5:30:65 MeOH:CHCl$_3$ saturated with NH$_3$: CH$_2$Cl$_2$)

EXAMPLE 17

Preparation of N-(2(R)-hydroxy-1(S)-indanyl)-trans-3-(3-pyridyl)acrylamide

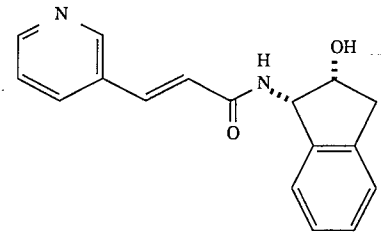

Using substantially the same procedure as for the preparation of N-(2(R)-hydroxy-1(S)-indanyl)-trans-3-(4-pyridyl)acrylamide, but substituting the appropriate starting materials, the title compound was prepared. Physical data: mp 119–120, Analysis Calculated for C$_{17}$H$_{16}$N$_2$O$_2$.0.65H$_2$O: C, 69.92; H, 5.97; N, 9.59. Found: C, 69.94; H, 5.74, N, 9.84.

EXAMPLE 18

Preparation of N-(1,2-N,O-isopropylidenen-2(R)-hydroxy-1(S)-indanyl)-trans-3-(3-pyridyl)acrylamide

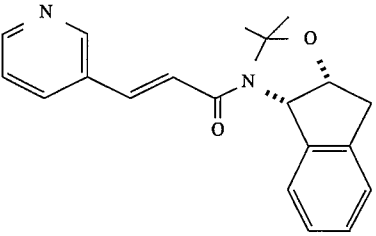

Using substantially the same procedure as for the preparation of N-(1,2-N,O-isopropylidenen-2(R)-hydroxy-1(S)-indanyl)-trans-3-(4-pyridyl)acrylamide, but substituting the appropriate starting material, the title compound was prepared. Physical data: mp 134–136, Analysis Calculated for C$_{20}$H$_{20}$N$_2$O$_2$.0.25H$_2$O: C, 73.94; H, 6.36; N, 8.62. Found: C, 73.95; H, 6.18, N, 8.70.

EXAMPLE 19

Preparation of N-(1,2-N,O-isopropylidenen-2(R)-hydroxy-1(S)-indanyl)-3-(3-pyridyl)propylamide

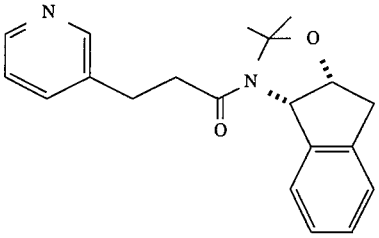

Using substantially the same procedure as for the preparation of N-(1,2-N,O-isopropylidenen-2(R)-hydroxy-1(S)-indanyl)-3-(4-pyridyl)propylamide, but substituting the appropriate starting material, the title compound was prepared.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for making a compound of formula I

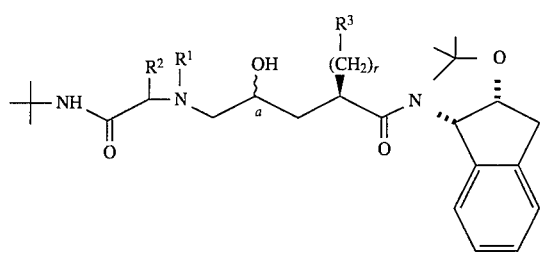

comprising reacting a compound of formula II

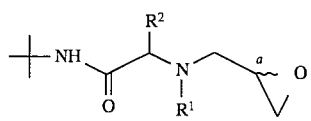

and an amide of formula VIII

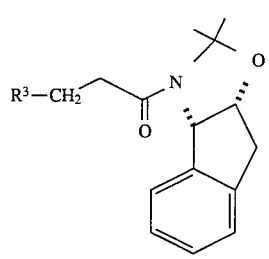

in the presence of a strong base at a low temperature; wherein:

stereocenter a is in either the R configuration, the S configuration or is racemic;

the strong base is selected from the group consisting of n-butyllithium, s-butyllithium, t-butyllithium, lithium diisopropylamide, lithium isopropylcyclohexylamide, lithium pyrrolidide, lithium tetramethylpiperidide, phenyllithium, isopropylmagnesium chloride, and isobutylmagnesium chloride;

the low temperature is in the range of about −82° C. to −40° C. to effect metalation of the amide VIII, and the temperature is in the range of about −50° C. to −10° C. to effect reaction of the metalated derivative of VIII and II:

$R^1$ and $R^2$ are joined together to form a cyclic structure selected from the group consisting of:

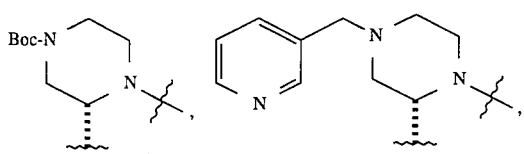

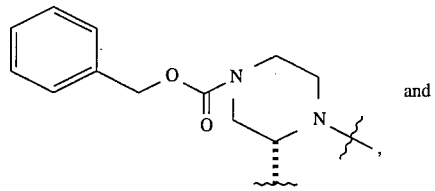

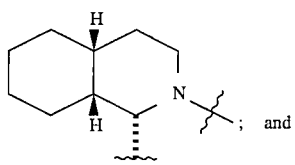

$R^3$ is selected from the group consisting of phenyl,

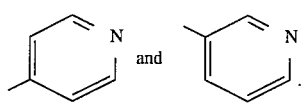

2. The process of claim 1 wherein the strong base is n-butyllithium, $R^3$ is phenyl, and $R^1$ and $R^2$ together are

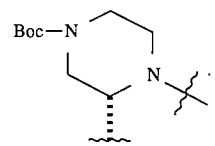

3. The process of claim 1 further comprising the step of producing the compound of formula II by reacting an amine of formula III

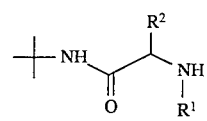

with a glycidol of formula IV

in the presence of base;

wherein G is a protecting group selected frown 3-nitrobenzenesulfonyl and trifluoromethanesulfonyl and $R^1$ and $R^2$ are as defined in claim 1.

4. The process of claim 3 wherein G is 3-nitrobenzenesulfonyl.

5. The process of claim 4 wherein the amine of formula III is (S)-2-tert-butylcarboxamide-4-tert-butoxycarbonylpiperazine.

6. The process of claim 5 further comprising the steps of (a) contacting a solution of (S)(R)-2-tert-butylcarboxamide-piperazine with an acid in an aqueous-organic solvent mixture, wherein the acid is selected from the group consisting of (+) or (−) tartaric acid, (+) or (−) mandelic acid, (+) or (−) dibenzoyltartaric acid, D or L-pyroglutamic acid, (+) or (−) di-O,O'-p-toluyl-tartaric acid, (+)or (−)malic acid, (+)or (−)-10-camphorsulfonic acid, (+) or (−)-3-bromo-10-camphorsulfonic acid, and (+) or (−)-3-chloro-10-camphorsulfonic acid;

(b) heating the mixture to dissolve any solid that forms;

(c) cooling the mixture;

(d) recovering (S)-2-tert-butylcarboxamide-piperazine as the precipitated crystals or from the mother liquor; and (e) treating the recovered (S) enantiomer with base followed by Boc₂O;

to produce the (S)-2-tert-butylcarboxamide-4-tert-butoxycarbonyl-piperazine.

7. The process of claim 1 further comprising the steps of
(a) reacting an amine of formula III

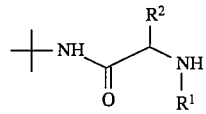

with a glycidol of formula V

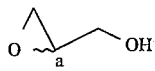

to produce a compound of formula VI

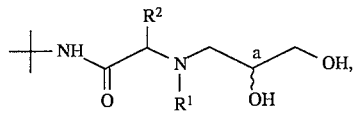

(b) treating VI with an activating agent selected from the group consisting of p-toluenesulfonyl chloride, methanesulfonyl chloride, and trifluoromethanesulfonic anhydride to produce VII

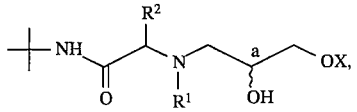

and (c) treating VII with a strong base to produce the compound of formula II;

wherein X is a group selected from p-toluenesulfonyl, methanesulfonyl, and trifluoromethanesulfonyl:

$R^1$ and $R^2$ are defined as in claim 1.

8. The process of claim 7 wherein the strong base in step (c) is selected from the group consisting of NaH, KOC(CH₃)₃, KOC(CH₃)₂CH₂CH₃, NaOC(CH₃)₂CH₂CH₃, lithium diisopropylamide, n-butyllithium, and lithium bis(trimethylsilyl)amide; and X is p-toluenesulfonyl.

9. A process for making a compound of formula II

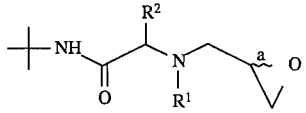

comprising reacting an amine of formula III

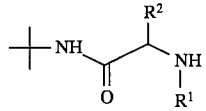

with a glycidol of formula IV

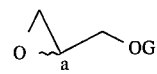

in the presence of base, said base selected from the group consisting of diisopropylethylamine, potassium carbonate, sodium carbonate, sodium bicarbonate, triethylamine, pyridine and dimethylaniline;

said reaction performed in a solvent selected from the group consisting of dimethylformamide, N-methyl pyrrolidinone, acetone, butanone, acetonitrile, tert-butyl alcohol, tert-amyl alcohol, 2-propanol, N-ethyl pyrrolidinone, 1,1,3,3-tetramethylurea, dimethylsulfoxide, 1,3-dimethyl-3,4,5,6-tetrahydro-2(1H)-pyrimidinone, tetramethylsulfone, tetrahydrofuran, 1,4-dioxane, pyridine and water, or combinations thereof; wherein stereocenter a is in either the R configuration, S configuration, or is racemic;

G is a protecting group and is 3-nitrobenzenesulfonyl; and $R^2$ are joined together to form a cyclic structure selected from the group consisting of:

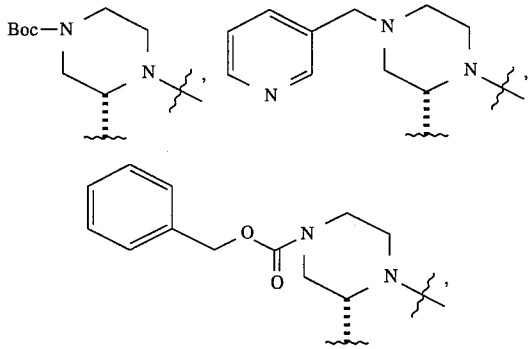

and

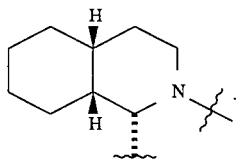

10. The process of claim 9 wherein the solvent is dimethylformamide and the base is diisopropylethylamine.

11. The process of claim 10 wherein $R^1$ and $R^2$ together are

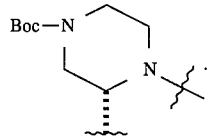

* * * * *